(12) United States Patent
Vallet (10) Patent No.: US 9,668,841 B2
(45) Date of Patent: Jun. 6, 2017

(54) TOOTHBRUSH HAVING A TERMINAL ROW OF BRISTLES OR SPIKES

(76) Inventor: Thierry André Christian Vallet, Saint Priest en Jarez (FR)

( * ) Notice: Subject to any disclaimer, the term of this patent is extended or adjusted under 35 U.S.C. 154(b) by 0 days.

(21) Appl. No.: 14/358,579

(22) PCT Filed: Nov. 16, 2011

(86) PCT No.: PCT/FR2011/052657
§ 371 (c)(1),
(2), (4) Date: Dec. 23, 2014

(87) PCT Pub. No.: WO2013/072570
PCT Pub. Date: May 23, 2013

(65) Prior Publication Data
US 2015/0101136 A1    Apr. 16, 2015

(51) Int. Cl.
*A61C 17/26* (2006.01)
*A46B 5/00* (2006.01)
(Continued)

(52) U.S. Cl.
CPC ............ *A61C 17/26* (2013.01); *A46B 5/0095* (2013.01); *A46B 15/0081* (2013.01);
(Continued)

(58) Field of Classification Search
CPC ..... A46B 13/001; A46B 13/02; A61C 17/222; A61C 17/24; A61C 17/26
(Continued)

(56) References Cited

U.S. PATENT DOCUMENTS 2,379,049 A  *  6/1945  Tompkins ............... A61C 17/26
15/22.1
2,662,238 A    12/1953  Robey
(Continued)

FOREIGN PATENT DOCUMENTS

CN    201244097 Y    5/2009
CN    201664348 U    12/2010
(Continued)

OTHER PUBLICATIONS

International Search Report, mailed Aug. 7, 2012 in connection with PCT Internationa Application No. PCT/FR2011/052657, filed Nov. 16, 2011.

*Primary Examiner* — Mark Spisich
(74) *Attorney, Agent, or Firm* — John P. White; Cooper & Dunham LLP (57) ABSTRACT

The invention relates to a toothbrush (1), in particular an electric toothbrush, comprising: —a support member (2), —a first tooth brushing member (3) mounted on said support member so as to be able to rotate about a rotation axis (XX'), said first brushing member having a lateral surface (3L) which extends along its rotation axis (XX') between a proximal end (3P) and an opposite distal end (3D), said lateral surface being intended to be brought into contact with the teeth (4) in order to clean them, said toothbrush being characterized in that it has a flexible trim (20), separate from the first brushing member (3), which is arranged facing the distal end (3D) approximately transversely to the rotation axis (XXI) so as to at least partially overlap the transverse section (3S) of said first brushing member (3).

19 Claims, 2 Drawing Sheets (51) Int. Cl.
*A46B 15/00* (2006.01)
*A61C 17/22* (2006.01)
A46B 9/02 (2006.01)
A61C 17/34 (2006.01)

(52) U.S. Cl.
CPC ............ *A61C 17/222* (2013.01); *A46B 9/025* (2013.01); *A46B 2200/1066* (2013.01); *A46B 2200/1086* (2013.01); *A61C 17/349* (2013.01)

(58) Field of Classification Search
USPC .................................................. 15/23, 25–27
See application file for complete search history.

(56) References Cited

U.S. PATENT DOCUMENTS

| | | | | |
|---|---|---|---|---|
| 2,662,239 | A | * 12/1953 | Grover | .................... A61C 17/26 |
| | | | | 15/23 |
| 3,015,833 | A | * 1/1962 | Gilet | ....................... A61C 17/26 |
| | | | | 15/23 |
| 2001/0022277 | A1 | * 9/2001 | Blaustein | ............... A61C 17/22 |
| | | | | 206/362.2 |
| 2005/0278874 | A1 | * 12/2005 | Blaustein | ............... A61C 17/22 |
| | | | | 15/22.1 |

FOREIGN PATENT DOCUMENTS

| FR | 2 930 135 A1 | 10/2009 |
|---|---|---|
| WO | WO 2006/055571 A2 | 5/2006 |

\* cited by examiner

TOOTHBRUSH HAVING A TERMINAL ROW OF BRISTLES OR SPIKES

CROSS-REFERENCE TO RELATED APPLICATIONS

This application is a §371 national stage of PCT International Application No. PCT/FR2011/052657, filed Nov. 16, 2011, the contents of which are hereby incorporated by reference in their entirety.

TECHNICAL FIELD

The present invention relates to the general field of dental hygiene instruments, and more particularly to the field of toothbrushes for human or veterinary use.

The present invention relates more particularly to a toothbrush comprising a support member of the handle type, and a first brush member for brushing teeth, which member is mounted to rotate on said support member about an axis of rotation (XX'), said first brush member having a side surface that extends along its axis of rotation (XX') between a proximal end facing towards the support member, and an opposite, distal end, said side surface being designed to be brought into contact with the teeth for the purpose of cleaning them.

PRIOR ART

Numerous types of electric toothbrush are known that are designed to improve brushing action, among which types are toothbrushes that have a brush member in the form of a rotary roller that approaches the face of the tooth tangentially, so as to perform a brushing movement in the direction going from the gum to the tooth.

Such toothbrushes are generally provided with retractors covering the brush member in part, away from the active zone in which the brush member comes into contact with the tooth, so as to form a screen between said brush member as it moves and the adjacent mucous membranes, and thus to avoid any irritation or injury thereto.

While such toothbrushes offer undeniable advantages, they can also sometimes suffer from certain drawbacks.

In particular, known retractors tend to hinder access by the brush member to the teeth, in particular in the narrow or remote zones of the mouth, and naturally that can be detrimental to the overall effectiveness of the brushing.

Furthermore, the presence of such known retractors generally significantly increases the volume occupied by the head of the toothbrush, and that additional volume is a source of discomfort during brushing.

In addition, the complexity of certain known toothbrushes tends to increase the cost of manufacturing them, sometimes tends to degrade their reliability due to the presence of mechanisms that are relatively fragile and that involve a large number of parts, and finally tends to make maintenance of them complicated and costly, e.g. if it becomes necessary to replace the entire head of the toothbrush even though some of its component elements are still in good order.

SUMMARY OF THE INVENTION

Objects assigned to the present invention are to remedy the above-mentioned drawbacks and to propose a novel toothbrush that has a particularly simple, compact, and inexpensive structure, and that enables brushing to be effective and comfortable.

Another object assigned to the invention is to propose a novel toothbrush that can easily access all of the zones of the mouth that need to be brushed.

Another object assigned to the invention is to propose a novel toothbrush that is particularly gentle both on the teeth and on the gums or on the adjacent mucous membranes, and that is particularly non-traumatic to use.

Another object assigned to the invention is to propose a modular toothbrush that is particularly easy to assemble and to maintain.

The objects assigned to the invention are achieved by means of a toothbrush comprising:

a support member, of the handle type; and a first brush member for brushing teeth, which member is mounted to rotate on said support member about an axis of rotation (XX'), said first brush member having a side surface that extends along its axis of rotation (XX') between a proximal end facing towards the support member, and an opposite, distal end, said side surface being designed to be brought into contact with the teeth for the purpose of cleaning them;

said toothbrush being characterized in that it is provided with a soft, covering that is distinct from the first brush member, and that is arranged facing the distal end of said first brush member, in axial alignment therewith, and substantially transversely to the axis of rotation (XX'), so as to extend at least part-way across the cross-section of said first brush member.

The objects assigned to the invention are also achieved by means of a replacement head for a toothbrush specific to the invention.

Finally, the objects assigned to the invention are achieved by a retractor for a toothbrush provided with a rotary brush member, said retractor being designed to cover in part the side surface of the rotary brush member of said toothbrush so as to protect the mucous membranes adjacent to the teeth from the action of said brush member, said retractor being provided with an axial recess designed to receive said brush member, said recess having a proximal access passage for passing the drive shaft that is designed to drive the brush member, said recess being edged by a protective wall, that is designed to cover the side surface of said brush member at least in part, along the axis of rotation, said retractor being characterized in that it has a soft covering that is disposed transversely to the axis of rotation (XX') in such a manner as to define the axial recess facing the distal end of the brush member, in axial alignment therewith, and in a manner such as to extend some way across the cross-section of said brush member.

BRIEF DESCRIPTION OF THE DRAWINGS

Other objects, characteristics and advantages of the invention appear in more detail on reading the following description and on examining the accompanying drawings that are given merely by way of non-limiting illustration, and in which.

BEST MANNER OF IMPLEMENTING THE INVENTION

The present invention relates to a toothbrush 1 designed to maintain dental hygiene by eliminating food deposits and dental plaque.

The present invention relates in particular to a toothbrush for human use, but it may equally be adapted to veterinary use, e.g. for farm animals or for pets.

In conventional manner, the toothbrush 1 has a support member 2 and at least one brush member 3 for brushing teeth.

In the meaning of the invention, the support member 2 enables the user to manipulate the brush member 3, and in particular substantially to control its position and its orientation in three dimensions, and to control the pressure with which it comes into contact with the teeth 4.

Naturally, the support member is in no way limited to any one particular embodiment, but it is preferably designed to make it possible to take hold of the toothbrush directly, and may, in particular, constitute a handle.

Preferably, said support member 2 is in the form of an elongate stick that is preferably circularly symmetrical in shape and that may optionally have a bulge 2A, followed axially by a constriction 213, and preferably by a wider bulb 2C that is, for example, substantially hemispherical, in such a manner that said support 2 has an ergonomic shape making it easier to take hold of.

In accordance with the invention, the brush member 3 is mounted to move in rotation on (and relative to) the support member 2, about an axis of rotation (XX').

Said brush member 3 has a side surface 313 that extends along its axis of rotation (XX') between a proximal end 3P that faces towards the support member 2, and an opposite, distal end 3D.

Said side surface 3L is designed to be brought into contact with the teeth so as to clean them, in this example by mechanical action constituted by abrasive brushing.

To this end, the brush member 3 preferably has soft elements, the geometrical envelope of which that covers the outside surface corresponds to said side surface 3L and is designed to come into contact with the teeth and with the gums.

Said soft elements of the first brush member may preferably be formed by a plurality of bristles or spikes, preferably made of a synthetic material, and projecting substantially radially relative to a core made of a rigid material and having its axis coinciding with the axis of rotation (XX').

Naturally, the diameter, the length, the shape, and the softness of the bristles or spikes are defined by the person skilled in the art as a function of the use for which the toothbrush is designed, and in particular as a function of the sensitivity of the user.

Naturally, the bristles or spikes of the first brush member may be disposed uniformly, optionally in tufts, they may be of equal length or of different lengths, and they may be mutually touching or spaced apart from one another, the physical surface of the brush member 3 then optionally having unevenness in its outline, e.g. an alternation of indentations and of projections, optionally interstices, or indeed a gouge or flute designed for removing the deposits.

For convenience of description, it is considered that, in the meaning of the invention, the side surface 3L refers to the geometrical envelope, lying between the proximal end 3P and the distal end 3D, and within which the soft elements covering the brush member 3 lie.

Preferably, said side surface 3L, and more particularly the brush member 3, is substantially circularly symmetrical in shape about the axis of rotation (XX'), or at least of shape that does not vary by rotation about said axis.

More particularly, the brush member 3 may be of substantially cylindrical shape, preferably of circular base, with a rectilinear generator line that corresponds to the axis (XX').

When the brush member 3 is formed by such a cylinder, the side surface 3L may advantageously correspond to the curved side wall of said cylinder, while the proximal end 3P and the distal end 3D may correspond to the plane circular base surfaces of said cylinder that are normal to the axis (XX').

Naturally, variations on the shape of the brush member are possible, it being possible for said brush member 3 to have a cross-section that is constant or that varies along the axis (XX'), and in particular to have an undulating profile, or to be egg-shaped or ellipsoidal with a proximal end 3D and a distal end 3D that form poles.

In addition, the length L of the brush member 3 is preferably significantly greater than its overall diameter $D_3$, it being possible, for example, for said length to lie in the range 15 millimeters (mm) to 30 mm, and preferably for it to be about 25 mm, while the overall diameter $D_3$ of its widest section may lie in the range 12 mm to 15 mm.

Advantageously, the brush member 3 forms a "longitudinally rotary" brush that makes it possible to perform tangential brushing of the teeth 4 using the "roll" or "rolling stroke" method, i.e. in a sweeping movement from the gum towards the tooth, that combines mechanically effective brushing with gentleness on the gums.

Figure 2:
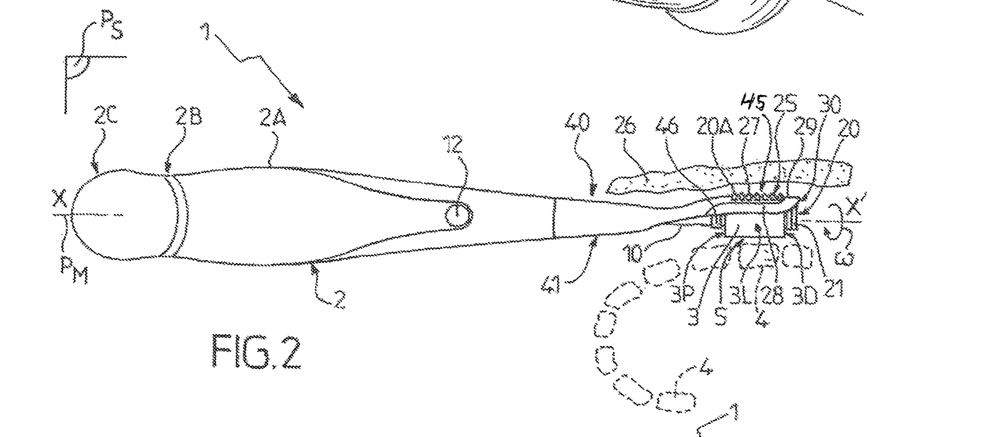
FIG. 2 is a side view of the toothbrush shown in FIG. 1.

In other words, the toothbrush 1 is arranged such that, during the brushing, the user can bring the side surface 3L of the brush member 3 in a tangential approach against the surface of the tooth 4, at an "active" zone 5, the axis of rotation (XX') then being substantially parallel to the main direction in which the gum and the face of the tooth being brushed extend, as shown diagrammatically in FIG. 2.

Preferably, the toothbrush 1 has a single rotary brush member 3, which, in particular, simplifies its structure and improves its compactness.

Advantageously, the toothbrush 1 of the invention is also provided with drive means 6 capable of driving the brush member 3 in rotation about its axis (XX') by transmitting to said brush member sufficient speed and torque to enable it to exert its mechanical action by friction on coming into contact with the teeth.

Figure 3:
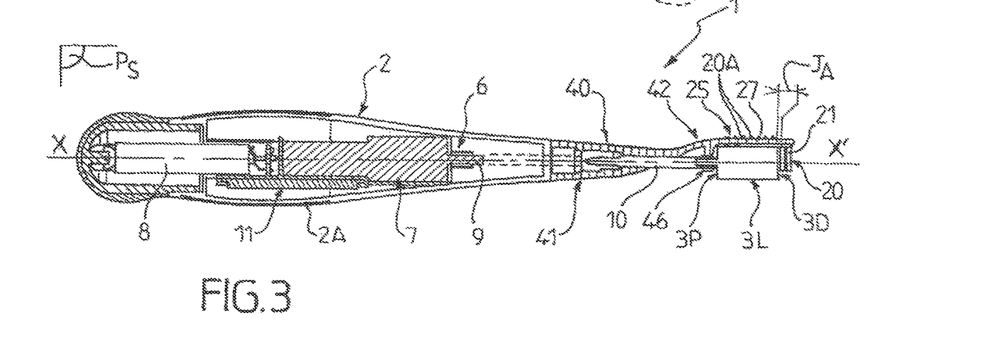
FIG. 3 is a section view, on the sagittal plane, of the toothbrush shown in FIG. 2.
Figure 4:
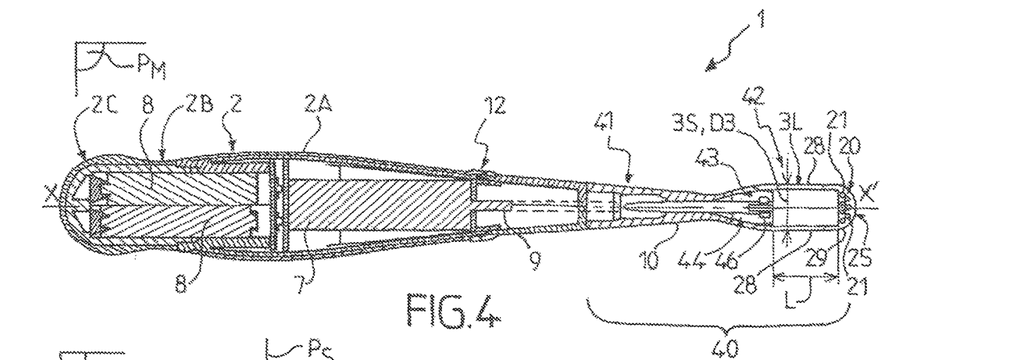
FIG. 4 is a section view, seen from below, on the midplane of the toothbrush, showing the toothbrush that is shown in FIGS. 1 to 3.
Figure 7:
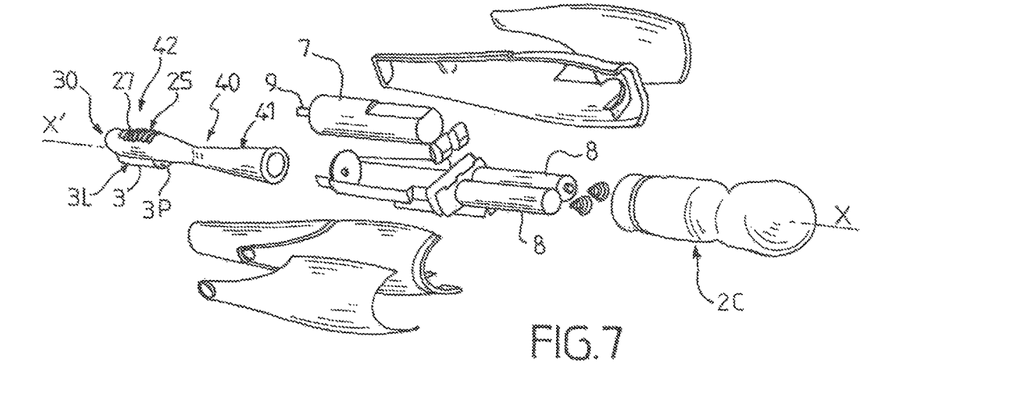
FIG. 7 corresponds to an exploded perspective view of the toothbrush shown in FIGS. 1 to 6.

In a preferred embodiment, shown in particular in FIGS. 3, 4, and 7, the drive means 6 may comprise an electric motor 7, powered by a rechargeable battery or by non-rechargeable batteries 8, and having its outlet shaft 9 in engagement with a transmission element 10 of the shaft or spindle type, itself connected to the brush member 3, and optionally formed integrally with the core carrying the bristles or spikes so as to form the tail of said brush member.

The toothbrush is thus an "electric" toothbrush in the sense that it is equipped with an electric motor that drives the brush member.

Preferably, the drive means 6 are arranged to drive the brush member 3 continuously, i.e. to enable said brush member to rotate through any number of consecutive turns in the same direction.

In addition, said drive means 6 are advantageously bi-directional, i.e. they are provided with reversal means enabling the user to chose, alternatively, one direction of rotation or the other direction of rotation for the brush member 3 about the axis (XX'), depending on whether the user is brushing the labial or the lingual faces of the teeth, and depending on whether the teeth are situated on the lower jaw or on the upper jaw.

Furthermore, the drive means 6 are preferably provided with a speed regulator designed to enable the user to choose the speed of rotation ω of the brush member 3, e.g. within the range 200 revolutions per minute (rpm) to 800 rpm, and more particularly within the range 300 rpm to 600 rpm.

Controlling the motor, and in particular selecting the direction of rotation or adjusting the speed of rotation may be performed by means of an electronic control card 11, the functions of which may advantageously be controlled, for example, by one or more buttons 12 accessible at the surface of the support 2. Advantageously, said control card 11 may be received in flat manner against a flat of the motor, substantially facing the bulge 2A, as is shown in FIGS. 3 and 4.

Figure 1:
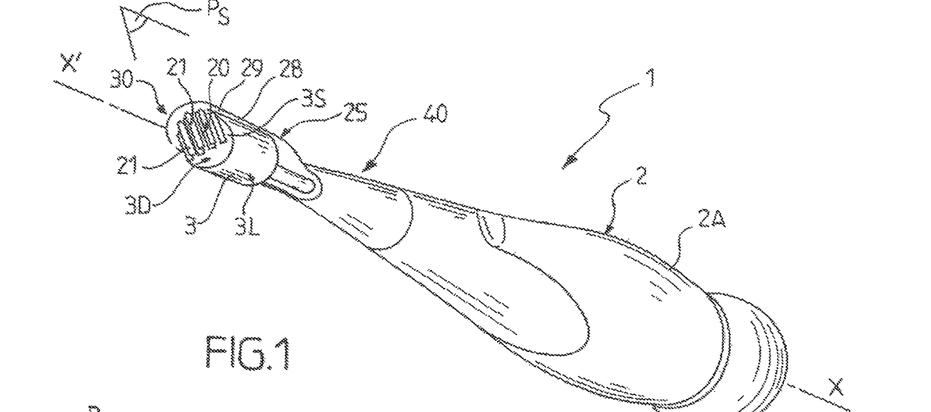
FIG. 1 is a perspective view of a variant embodiment of a toothbrush of the invention.
Figure 5:
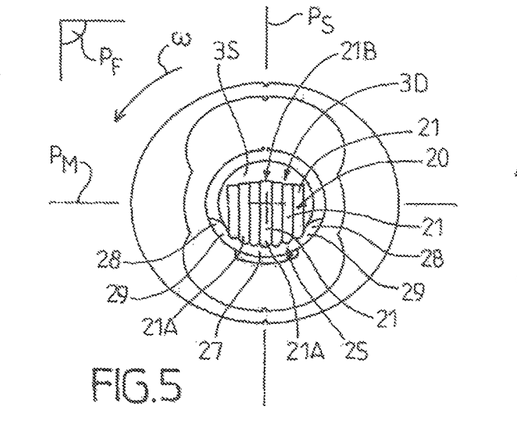
FIG. 5 is a side view of the toothbrush shown in FIGS. 1 to 4.

In accordance with an important characteristic of the invention, the toothbrush 1 is provided with a soft covering 20 that is distinct from the first brush member 3, said soft covering 20 being arranged facing the distal end 3D of said first brush member 3, in axial alignment therewith, and substantially transversely to the axis of rotation (XX'), so as to extend at least part-way across the cross-section 3S of said first brush member 3, as is shown, in particular, in FIGS. 1, 2, and 5.

The soft covering 20 thus hangs in the manner of a curtain or of a soft and more particularly flexible protective screen disposed in the vicinity of the distal end of the toothbrush, axially beyond the first rotary brush member 3, and thus at least partially covering and masking the distal end 3D of said brush member.

Advantageously, such a construction configuration makes it possible to obtain better protection, the soft covering 20 offering coverage of the brush member at a zone of it that is a priori non-operative, in order to prevent said non-operative zone from interfering with the mucous membranes 26, while also being soft, and therefore being gentle on the tissues and procuring comfortable brushing.

Said soft covering 20 may preferably form a second brush member having dimensions, shapes, and component materials that can advantageously be adapted to suit the brushing.

Advantageously, the soft covering 20 is drivingly distinct from the first brush member 3, and, particularly preferably, is fastened in a substantially unvarying position (ignoring any deformation in it) relative to the support member 2.

Preferably, the soft, covering 20 is made up of a plurality of advantageously flexible bristles or spikes, or of tufts of advantageously flexible bristles or spikes 21, or of a series of advantageously flexible spikes extending or formed integrally with the soft material forming the soft covering 20, which bristles, spikes, tufts or series are preferably arranged in one or more rows that are preferably substantially normal to the axis of rotation (XX').

More particularly, as shown, in particular, in FIGS. 1 to 4, the soft covering 20 may comprise two or more rows of tufts of bristles or spikes made of a soft material and in succession axially, and preferably forming a sort of boat shape or bow that, in the midplane $P_M$ of the toothbrush 1, as shown in FIG. 4, forms an overall outline that is rounded in its distal portion, and that is preferably crescent-shaped, thereby improving the esthetic appearance and the non-traumatic aspect of the soft covering and of the toothbrush as a whole.

For convenience of description, the term "sagittal plane" $P_S$ is used to designate the plane containing the axis of rotation (XX') and that geometrically divides the toothbrush into a left half and a right half that are substantially symmetrical to each other, said plane being substantially vertical in FIGS. 2 and 3, the term "midplane" $P_M$ is used to designate the plane that contains the axis of rotation (XX'), that is substantially perpendicular to the sagittal plane $P_S$, and that divides the toothbrush, and more particularly the brush member 3 into a "ventral" lower portion, in which the active zone 5 is situated, and a "dorsal" opposite upper portion, and finally the term "frontal plane" $P_F$ or "transverse plane" is used to designate the plane that is substantially perpendicular to the preceding planes and that is substantially normal to the axis of rotation (XX').

Preferably, the bristles or spikes 21, and more generally the rows of bristles or spikes or the covering 20 as a whole may extend substantially in said frontal plane $P_F$, and in particular be contained in a plane that is substantially normal to the axis of rotation (XX').

However, at rest, i.e. independently of any bending in operation on coming into contact with the teeth 4, it is not excluded that the bristles or spikes, or tufts of bristles or spikes 21 might be inclined to some extent, e.g. inclined to in the range 5 degrees to 10 degrees, or indeed to 20 degrees or 30 degrees, relative to said normal.

In addition, an empty interstice is preferably provided between the distal end 3D of the brush member and the surface of the soft covering 20 that is axially closer to it, so as to form axial clearance $J_A$ between these elements, in particular in order to avoid premature wear on the distal end of the brush member and/or on the covering.

In addition, the soft covering 20 preferably forms a screen that, in projection in a plane $P_F$ normal to the axis of rotation, as is shown, in particular in FIG. 5, covers at least 20%, at least 30%, at least 50%, or indeed at least 75% or 80% of the area occupied by the brush member 3 in projection in the same plane.

In other words, in the frontal plane $P_F$, the soft covering 20 preferably has a percentage of cross-sectional area coverage that corresponds to the above-mentioned values, so as to mask effectively the non-operative portion of the proximal end 3P of the brush member, and more particularly at least one third, one half, or indeed two-thirds or three-quarters of the upper "dorsal" sector of the disk within which said brush member lies (in projection in said frontal plane), all this while allowing easy and comfortable access to the operative portion of said brush member 3.

To this end, the length of the bristles or spikes 21 of the covering, as measured between their roots 21A and their free ends that point towards to the active zone 5, may have proportions analogous to those mentioned above regarding the diameter $D_3$ of the roller forming the brush member.

Preferably, the free ends 21B of said bristles or spikes are, however, situated set back from the gauge plane that is parallel to the midplane and that extends tangentially to the brush member 3 at the active zone 5, so as to procure a general protection effect and so as to allow the lower portion to appear freely, and in particular the bottom third or the bottom quarter (fourth) of said active zone 5, as is shown in particular in FIGS. 2, 3, and 5.

In addition, as shown in the figures, the axis of rotation (XX') is preferably substantially parallel to, and particularly preferably coincides with, the main direction in which the handle 2 extends longitudinally, thereby procuring good grip and a brushing gesture that is very intuitive.

Preferably, the toothbrush 1 is also provided with a retractor 25 that covers in part the side surface 3L of the brush member 3, so as to protect the mucous membranes 26 adjacent to the teeth 4 from the action of said brush member 3, while said brush member is being moved in rotation, as shown in FIG. 2.

Advantageously, said retractor 25 is drivingly independent from the brush member 3 so as not, itself, to be driven in rotation by the drive means 6.

In addition, said retractor 25 is preferably fastened in an unvarying position on the support member 2.

Preferably, the soft covering 20 may then be fastened to said retractor 25, in a distal portion thereof, axially situated beyond the distal end 3D of the first brush member 3.

More particularly, the bristles or spikes 21 may be implanted or rooted in a dorsal wall element 27 of said retractor, which element is situated substantially opposite from the active zone 5 relative to the midplane $P_M$, at an axial abscissa position that is further away than the axial abscissa position of the movable brush member 3, and more particularly beyond an interstice axially fitting over the distal end 3D of said brush member 3, the covering 20 thus forming one or more end rows of bristles or spikes at the distal end of the toothbrush.

Preferably, in addition to the dorsal wall element 27, the retractor 25 has side cheeks 28 that are situated axially set back towards the handle 2 relative to the distal end of said dorsal wall element 27, and closer to the active zone 5 of the toothbrush 1 than said dorsal wall element, and the retractor 25 also has substantially slanting engagement ramps 29 that connect the dorsal wall element 27 to said cheeks 28 by descending towards the active zone 5 in the direction of decreasing axial abscissae positions (i.e. from the distal portion towards a more proximal portion), so as to form a beveled tip 30.

Advantageously, this bevel, that rises up from the side cheeks 28, in order to narrow and to reduce progressively, along the axis of rotation (XX'), the angular coverage procured by the retractor 25 in azimuth about said axis, to the free distal end of said retractor, makes it possible to uncover at least or in part the brushing element(s), and to facilitate access thereto, while protecting the mucous membranes 26 effectively.

Preferably, the engagement ramps 29 have rounded and preferably convex outlines, the retractor being substantially spoon-shaped, so as to enable said retractor and the toothbrush 1 to penetrate gently into the mouth, between the teeth and the mucous membrane, by a softened wedging effect.

In a variant embodiment shown in the figures, the side cheeks 28 may have outlines that are substantially truncated and that extend substantially along the axis of rotation (XX'), preferably a little above the midplane $P_M$, so as to uncover at least part of and preferably the majority of the lower portion of the side surface 3L of the brush member, it being possible for the angular coverage of the retractor at said cheeks 28 to lie substantially in the range 90° to 120°, or indeed 150° about the axis (XX').

However, it is also possible for said cheeks 28 to extend down to the level of the midplane $P_M$, or even to below said level, i.e. to come closer to the active zone 5 by wrapping around the brush member 3 over an angular coverage that can exceed 180 degrees or even 190 degrees.

Figure 6:
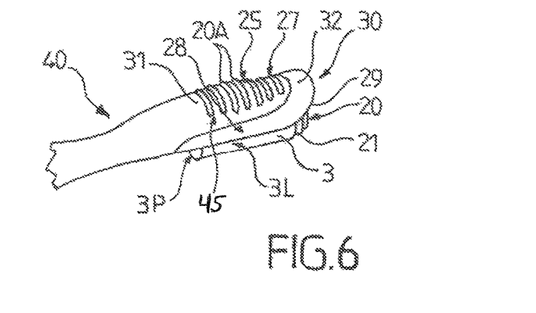
FIG. 6 is a perspective fragmentary detail view of the head of the toothbrush shown in the preceding figures.

In addition, in accordance with a preferred characteristic that may constitute an invention in its own right, regardless of the arrangement of the toothbrush 1, of the brush member 3, or even independently of the presence of a covering 20, the retractor 25 may, as is shown, in particular, in FIG. 6, have a body portion 31 forming a rigid or semi-rigid protective wall, and also a margin 32 that surrounds said body portion 31 at the free edge faces of the retractor, and in particular along the engagement ramps 29 and/or the cheeks 28, said margin 32 being softer that said body portion 31.

Advantageously, the retractor 25 may thus have a two-material structure, the body portion 31 that, preferably forms the central framework of the retractor, and in particular at least the dorsal portion 27 designed to withstand, in substantially "flat" manner, the retraction force for retracting the mucous membranes 26, being made of a first rigid or semirigid material, while the peripheral portions, and in particular the edge faces of the retractor that might, in particular, come into contact via their sharp edges with the gums or with the teeth while the toothbrush is penetrating into the mouth or is being manipulated, are provided with a protective margin 32 made of a second material that is softer than the first material.

Such a two-material structure that advantageously enables the retractor 25 firstly to hold the mucous membranes effectively and to retract them securely, and secondly to have a gentle and non-traumatic nature during the penetration or positioning movements, may, in particular, be formed by overmolding or by any other equivalent technique.

Preferably, the margin 32 may be in the form of a lip, of a skirt, or of a flap that is relatively soft, and more particularly flexible, and that edges the rigid body portion 31 forming a shell. In addition, it may have rounded extra thickness, of the bead or tube type, improving the non-traumatic nature of the free edges of the retractor.

Furthermore, the soft covering 20 is preferably axially disposed substantially facing the engagement ramps 29, as is shown, in particular in FIG. 2.

In accordance with a preferred characteristic, the first rotary brush member 3 is mounted axially in cantilevered-out manner.

The distal end of the toothbrush 1, and more particularly of the retractor 25, may then, in particular be free from any rigid wall transverse to the axis, or at least from any bearing designed to support the drive shaft 10 facing the distal end 3D of the brush member, it thus being possible for said distal end to be uncovered, i.e. not covered by a rigid screen, in projection in the frontal plane, over at least one half, two-thirds, three-quarters, or even the whole of its height.

Preferably, the soft covering 20 may then be used to mask the distal terminal portion of the shaft 10 that supports and drives said brush member.

Furthermore, the soft covering 20 that can form the outside surface of the retractor 25 may have pieces in relief, and in particular projecting ribs 20A that are substantially mutually parallel and that extend transversely to the axis XX', as shown in particular in FIGS. 2, 3, and 6 in order to form means for brushing the tongue. The retractor 25 is thus provided with ribs 20A forming means for brushing the tongue.

Naturally, the invention also relates per se to a replacement head 40 for a toothbrush 1, it being advantageously possible for said head to be mounted removably on the support 2, by appropriate connection means, and, for example, by screw-fastening, interfitting, bayonet-type fastening, or snap-fastening.

Advantageously, such a replacement head 40 may be used to replace a worn head, or as a retrofit on a prior art toothbrush in order to transform that toothbrush into a toothbrush 1 of the invention.

In accordance with the invention, said replacement head 40 may comprise a first brush member 3 for brushing teeth 4, which member is mounted to rotate about an axis of rotation (XX'), said first brush member 3 having a side surface 3L that extends along its axis of rotation (XX') between a proximal end 32 facing towards the support member 2 on which the head 40 is designed to be mounted, and an opposite, distal end 3D, said side surface being designed to be brought into contact with the teeth 4 for the purpose of cleaning them, said replacement head 40 being provided with a soft covering 20 that is distinct from the first brush member 3, and that is arranged facing the distal end 3D of said first brush member 3, in axial alignment therewith, and substantially transversely to the axis of rotation (XX'), so as to extend at least part-way across the cross-section of said first brush member.

Advantageously, said replacement head 40 carries the brush member 3, preferably with its drive spindle 10, and the retractor 25 supporting the bristles or spikes 21, and thus forms a subassembly that is easy to mount on, to remove from, or to adapt to fit one or more types of toothbrush support 2.

Naturally, the component members of the replacement head 40 may have all or some of the above-described characteristics.

As shown in the figures, said head 40 may have a proximal first portion 41 designed to be coupled to the support 2 and preferably having a constriction, e.g. in the form of a truncated cone whose large base fits over said support 2, said proximal portion being followed, in the direction of increasing abscissae positions, by a distal portion 42, that is preferably formed integrally with said proximal portion 41, it being possible for said distal portion 41 to form the retractor 25 and more particularly the rigid body 31 thereof, which body flares from the constriction corresponding to the apex of the truncated cone.

Naturally, the present invention also relates, per se, to a retractor 25 for a toothbrush provided, with a rotary brush member 3, said retractor 25 being designed to cover in part the side surface 3L of the rotary brush member 3 of said toothbrush 1 so as to protect the mucous membranes 26 adjacent to the teeth 4 from the action of said brush member 3.

To this end, said retractor 25 is advantageously provided with an axial recess 43 designed to receive said brush member 3, said recess advantageously being open at least in part in its lower portion, by forming a window allowing at least a portion of said brush member 3 to appear, and preferably to project from said recess, under the midplane and at the active zone 5.

Advantageously, said axial recess 43 has a proximal access passage 44 for passing the drive shaft, and more particularly for passing the spindle 10, which shaft and spindle are designed to drive the brush member 3 in rotation, said recess 43 also being edged by a protective wall that is preferably substantially cylindrical, and that is designed to cover the side surface 31 of said brush member 3 at least in part, along the axis of rotation (XX').

Preferably, said protective wall 45 corresponds to the assembly formed by the dorsal wall 27 and by the cheeks 28 that are described above.

In particularly advantageous manner, said retractor 25 has a soft covering 20 that is disposed transversely to the axis of rotation (XX') in such a manner as to define the axial recess 43 facing the distal end 3D of the brush member 3, in axial alignment therewith, and in a manner such as to extend some way across the cross-section 3S of said brush member 3.

Naturally, the various component elements of said retractor may have all or some of the above-described characteristics.

Preferably, the axial recess 43 may thus be in the form of a recess that is substantially tubular and cylindrical, centered on the axis of rotation (XX'), advantageously free of any rigid wall or of any bearing in its distal portion that advantageously remains open, and preferably beveled, but that is nevertheless closed off at least in part by the soft covering 20, and in particular by one or more rows of advantageously flexible bristles or spikes 21 that mark the distal limit of said recess the furthest away from said handle 2 and the closest to the use when the toothbrush penetrates into the mouth.

Advantageously, the retractor 25, and more generally the head 40 may, preferably in the vicinity of the proximal access passage 44, be provided with a bearing 46, preferably of the smooth bearing type, designed to receive the drive spindle 10 of the brush member 3 and to guide it in rotation.

Advantageously, such a construction configuration makes it possible to limit, the extent to which said member 3 is cantilevered out, preferably by limiting that extent substantially to the length L of said brush member 3, ignoring operating axial clearance. It also makes it possible to hold the member 3 and the shaft 10 in place relative to said retractor 25, by stabilizing them, and by enabling them, in particular, to withstand better the bending or radial penetration forces exerted transversely by the tooth on the brush member 3, in reaction to the brushing pressure.

Advantageously, said bearing 46 may be in the form of a substantially circular hole provided at the free end of a tongue bearing against, the inside face of the dorsal wall 27, and preferably formed integrally with the retractor and more particularly with its rigid body 31, as is visible, in particular, in FIG. 3.

Finally, said retractor 25 may advantageously be provided with a foot extending beyond the axial recess 43 along the axis of rotation, and preferably forming a hollow truncated cone corresponding to the proximal portion 41 of the head 40, said foot advantageously offering a casing that conceals and optionally guides the spindle 10.

Thus, the toothbrush of the invention, and its various accessories, such as the replacement head 40 and the retractor 25, advantageously procure brushing that is particularly safe, comfortable, and non-traumatic, during which the user can readily access all of the mouth zones that are to be cleaned, and can approach the teeth successively via their various faces, always by using the roll method. Advantageously, depending on the brushing configuration, and more particularly depending on the face being brushed, the direction and the speed of rotation may be adapted and controlled by the user.

Advantageously, the soft covering offers non-constraining protection of the mucous membranes, of the gums, or indeed of the teeth themselves, from the brush member 3, and more particularly from the end of the shaft 10 that drives the brush member in rotation, in such a manner that, by means of the retractor 25, only the operating portion of the brush member 3 is accessible and can reach the teeth and act thereon in a brushing movement consistent with the roll method.

As and when necessary, the bristles or spikes 21 of the soft covering 20 no not form a hard obstacle that might bump into the teeth or the gums, but rather a sort of flexible curtain that is suitable for bending, in particular towards the member and/or away therefrom so as to make it possible, as do the engagement ramps 29, to procure gentle and progressive access for the brush member 3 to the zone to be brushed.

In addition, the simplicity and the small number of elements implemented, and in particular the small number of movable elements implemented, enables lightness and compactness to be improved, and also enables the toothbrush to be manufactured, assembled, or removed easily, while allowing selective replacement of only those elements that are worn or damaged, thereby limiting the cost of manufacturing and maintaining said toothbrush.

SUSCEPTIBILITY OF INDUSTRIAL APPLICATION

The invention is industrially applicable to manufacturing toothbrushes, in particular electric toothbrushes.

The invention claimed is:
1. A toothbrush (1) comprising:
    a support member (2), of the handle type; and
        a first brush member (3) for brushing teeth, which member is mounted to rotate on said support member about an axis of rotation (XX'), said first brush member having a side surface (3L) that extends along its axis of rotation (XX') between a proximal end (3P) facing towards the support member, and an opposite, distal end (3D), said side surface being designed to be brought into contact with the teeth (4) for the purpose of cleaning them;
        wherein said toothbrush is provided with a soft covering (20) that is distinct from the first brush member (3), and that is arranged facing the distal end (3D) of said first brush member, in axial alignment therewith, and substantially transversely to the axis of rotation (XX'), so as to extend at least part-way across the cross-section (3S) of said first brush member (3),
        wherein said toothbrush further comprising a sagittal plane ($P_S$) containing the axis of rotation (XX') and dividing geometrically the toothbrush (1) into a left half and a right half, and a midplane ($P_M$) containing the axis of rotation (XX'), said midplane ($P_M$) being substantially perpendicular to the sagittal plane ($P_S$) and dividing the toothbrush (1) into a ventral lower portion and a dorsal opposite upper portion,
        wherein said toothbrush further comprising a retractor (25) covering the side surface (3L) of the first brush member (3) at least in part so as to protect the mucous membranes (26) adjacent to the teeth (4) from the action of said brush member (3),
    wherein said retractor (25) comprising a dorsal wall element (27) and side cheeks (28) situated axially set back towards the handle relative to the distal end of said dorsal wall element (27), and closer to an active zone (5) of the toothbrush (1) than said dorsal wall element (27),
    wherein said side cheeks (28) having outlines extending substantially along the axis of rotation and above the midplane ($P_m$), so as to uncover at least the majority of the lower portion of the side surface (3L).

2. The toothbrush according to claim 1, wherein the soft covering (20) is stationary relative to the support (2).

3. The toothbrush according to claim 2, wherein the soft covering (20) comprises a plurality of bristles or spikes, or of tufts of bristles or spikes (21), arranged in one or more rows substantially normal to the axis of rotation (XX').

4. The toothbrush according to claim 2, wherein the soft covering (20) forms a screen that, in projection in a plane ($P_F$) normal to the axis of rotation, covers at least 20% of the area (3S) occupied by the brush member in projection in the same plane.

5. The toothbrush according to claim 2, wherein the soft covering (20) forms a second brush member.

6. The toothbrush according to claim 1, wherein the soft covering (20) comprises a plurality of bristles or spikes, or of tufts of bristles or spikes (21), arranged in one or more rows substantially normal to the axis of rotation (XX').

7. The toothbrush according to claim 6, wherein the soft covering (20) forms a screen that, in projection in a plane ($P_F$) normal to the axis of rotation, covers at least 20% of the area (3S) occupied by the brush member in projection in the same plane.

8. The toothbrush according to claim 1, wherein the soft covering (20) forms a screen that, in projection in a plane ($P_F$) normal to the axis of rotation, covers at least 20% of the area (3S) occupied by the brush member in projection in the same plane.

9. The toothbrush according to claim 1, wherein the soft covering (20) forms a second brush member.

10. The toothbrush according to claim 1, wherein the soft covering (20) is fastened to said retractor (25), in a distal portion thereof that is situated axially beyond the distal end (3D) of said first brush member (3).

11. The toothbrush according to claim 10, wherein the retractor (25) further comprises substantially slanting engagement ramps (29) that connect the dorsal wall element (27) to said cheeks (28) by descending towards the active zone (5) in the direction of decreasing axial abscissae positions, so as to form a beveled tip (30).

12. The toothbrush according to claim 11, wherein the soft covering (20) is disposed axially facing the engagement ramps (29).

13. The toothbrush according to claim 10, wherein the retractor (25) is provided with ribs (20A) forming means for brushing the tongue.

14. The toothbrush according to claim 10, wherein the retractor (25) firstly has a body portion (31) forming a rigid or semi-rigid protective wall and secondly a margin (32) that surrounds said body portion at the free edge faces of the retractor (25), and that is softer than said body portion.

15. The toothbrush according to claim 1, wherein the toothbrush has a single rotary brush member (3).

16. The toothbrush according to claim 1, wherein the axis of rotation (XX') is substantially parallel to and preferably substantially coincides with the main direction in which the handle (2) extends.

17. The toothbrush according to claim 1, wherein the first rotary brush member (3) is mounted axially in cantilevered out manner, and wherein the soft covering (20) masks a distal end portion of a shaft (10) that supports said brush member.

18. The toothbrush according to claim 1, a continuous drive means (6) designed to drive the first brush member (3) in rotation about the axis (XX') through any number of turns in the same direction.

19. A replacement head (40) for a toothbrush (1), said replacement head comprising a first brush member (3) for brushing teeth, which member is mounted to rotate about an axis of rotation (XX'), said first brush member having a side surface (3L) that extends along its axis of rotation (XX') between a proximal end (3P) facing towards a support member (2) of the toothbrush (1) on which the head (40) is designed to be mounted, and an opposite, distal end (3D), said side surface being designed to be brought into contact with the teeth (4) for the purpose of cleaning them, wherein the replacement head (40) is provided with a soft covering (20) that is distinct from the first brush member (3), and that is arranged facing the distal end of said first brush member (3), in axial alignment therewith, and substantially transversely to the axis of rotation (XX'), so as to extend at least part-way across the cross section (35) of said first brush member, wherein said toothbrush further comprising a sagittal plane ($P_S$) containing the axis of rotation (XX') and dividing geometrically the toothbrush (1) into a left half and a right half, and a midplane ($P_M$) containing the axis of rotation (XX'), said midplane ($P_M$) being substantially perpendicular to the sagittal plane ($P_S$) and dividing the toothbrush (1) into a ventral lower portion and a dorsal opposite upper portion, wherein said replacement head (40) further comprising a retractor (25) covering the side surface (3L) of the first brush member (3) at least in part so as to protect the mucous membranes (26) adjacent to the teeth (4) from the action of said brush member (3), wherein said retractor (25) further comprising a dorsal wall element (27) and side cheeks (28) situated axially set back towards a handle of the support member (2) relative to the distal end of said dorsal wall element (27), and closer to an active zone (5) of the toothbrush (1) than said dorsal wall element (27), wherein said side cheeks (28) having outlines extending substantially along the axis of rotation and above the midplane ($P_m$), so as to uncover at least the majority of the lower portion of the side surface (3L).

* * * * *